United States Patent [19]

Morita et al.

[11] Patent Number: 4,607,046
[45] Date of Patent: Aug. 19, 1986

[54] 4-(1-IMIDAZOLYLMETHYL)CINNAMIC ACID HYDROCHLORIDE MONOHYDRATE AND PHARMACEUTICAL COMPOSITIONS

[75] Inventors: Kaname Morita; Shigeo Arikawa; Mitsuo Watanabe; Kinji Iizuka; Kenji Akahane, all of Nagano, Japan

[73] Assignees: Kissei Pharmaceutical Co., Ltd.; Ono Pharmaceutical Co., Ltd., both of Japan

[21] Appl. No.: 347,616

[22] Filed: Feb. 10, 1982

[30] Foreign Application Priority Data

Feb. 10, 1981 [JP] Japan .................. 56-18488

[51] Int. Cl.$^4$ .................. A61K 31/415; C07D 233/60
[52] U.S. Cl. ...................... 514/399; 548/335
[58] Field of Search .................. 548/335; 424/273 R; 514/399

[56] References Cited
U.S. PATENT DOCUMENTS 4,226,878 10/1980 Iizuka et al. .................. 548/335

OTHER PUBLICATIONS

Ogata et al., *Kagaku Jikken Sosaho*, (1958), pp. 403, 414, 415.

*Primary Examiner*—Robert W. Ramsuer
*Attorney, Agent, or Firm*—Sughrue, Mion, Zinn, Macpeak and Seas

[57] ABSTRACT

4-(1-Imidazolylmethyl)cinnamic acid hydrochloride monohydrate of the formula:

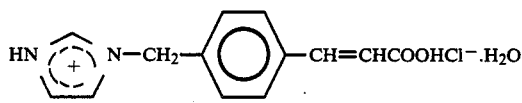

and pharmaceutical compositions containing such compound.

The imidazole derivative above has a strong and specific inhibitory effect on thromboxane synthetase from human or bovine platelet microsomes, and is useful as a therapeutical agent for inflammation, hypertension, thrombus, cerebral apoplexy, and asthma.

3 Claims, No Drawings

4-(1-IMIDAZOLYLMETHYL)CINNAMIC ACID HYDROCHLORIDE MONOHYDRATE AND PHARMACEUTICAL COMPOSITIONS

BACKGROUND OF THE INVENTION

1. Field of the Invention

The present invention relates to novel imidazole derivative. More particularly, the present invention relates to 4-(1-imidazolylmethyl)cinnamic acid hydrochloride monohydrate of the formula (I):

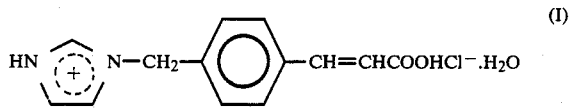

and to pharmaceutical compositions containing such compound.

2. Description of the Prior Art

It has been reported that 4-(1-imidazolylmethyl)cinnamic acid and its pharmaceutically acceptable salt possess a strong and specific inhibitory action for biosynthesis of thromboxane $A_2$ and are useful for the treatment of diseases caused by thromboxane $A_2$ such as inflammation, hypertension, thrombus, cerebral apoplexy, and asthma [U.S. Pat. No. 4,226,878]. However the former compound, i.e. free compound, is amphosteric and is hard to be isolated and purified. The latter compound, i.e. salt compound, has highly hygroscopic property and the water contained in said compound varies depending upon moisture in atmosphere in which said compound is allowed to stand. Accordingly, a net weight of said compound tends to vary due to its hygroscopic property by absorbing moisture from atmosphere and taking into consideration that a pharmaceutical composition has always to contain an active agent at a prescribed ratio so as to achieve the expected effects and safety, said compound is not necessarily desirable for preparing pharmaceutical compositions.

From an extensive research and experimentation, we found that such problem was absolutely solved by using the compound of the formula (I) above. That is, the compound of the formula (I) is non-hygroscopic and has a constant net weight without being affected by moisture contained in atmosphere.

SUMMARY OF THE INVENTION

Accordingly, an object of this invention is to provide a compound which exhibits a strong and specific inhibitory effect on thromboxane synthetase and which is therapeutically useful.

Another object of this invention is to provide 4-(1-imidazolylmethyl)cinnamic acid hydrochloride monohydrate having non-hygroscopic property.

Yet another object of this invention is to provide pharmaceutical compositions comprising 4-(1-imidazolylmethyl)cinnamic acid hydrochloride monohydrate of the formula (I).

A further object of this invention is to provide methods for the treatment of diseases such as inflammation, hypertension, thrombus, cerebral apoplexy, and asthma using 4-(1-imidazolylmethyl)cinnamic acid hydrochloride monohydrate of the formula (I).

Other objects, features and advantages of this invention will become more apparent from the following description of the invention.

DETAILED DESCRIPTION OF THE INVENTION

The present invention provides 4-(1-imidazolylmethyl)cinnamic acid hydrochloride monohydrate of the formula (I):

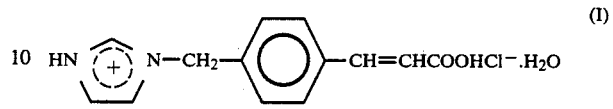

and the pharmaceutical compositions containing such compound.

Specifically, the present invention relates to 4-(1-imidazolylmethyl)cinnamic acid hydrochloride monohydrate having no inexpedient property in the preparation of pharmaceutical composition, such as hygroscopic property of 4-(1-imidazolylmethyl)cinnamic acid salt and having a strong and specific inhibitory effect on biosynthesis of thromboxane $A_2$ in mammalia including human.

That is, 4-(1-imidazolylmethyl)cinnamic acid hydrochloride monohydrate of the formula (I) has no hygroscopic property and is stable below about 50° C. under high or low humidity condition. Accordingly this compound has always a constant net weight without being affected by moisture contained in atmosphere and using 4-(1-imidazolylmethyl)cinnamic acid hydrochloride monohydrate, pharmaceutical compositions can easily be prepared and the obtained pharmaceutical compositions can be of high quality. Furthermore, 4-(1-imidazolylmethyl)cinnamic acid hydrochloride monohydrate possesses a specific and strong inhibitory effect substantially equal to 4-(1-imidazolylmethyl)cinnamic acid and its salt on biosynthesis of thromboxane $A_2$.

The term "aqueous organic solvent" as used in this invention means an organic solvent wherein water content is more than 5% (V/V%).

4-(1-Imidazolylmethyl)cinnamic acid hydrochloride monohydrate of the formula (I) of this invention can easily be prepared by recrystallizing 4-(1-imidazolylmethyl)cinnamic acid hydrochloride from an adequate recrystallization solvent.

In this process, water and aqueous organic solvents can be employed as a recrystallization solvent. Examples of aqueous organic solvents include aqueous methanol, aqueous ethanol, aqueous propanol, aqueous acetone, aqueous methylethylketone, aqueous dioxane, etc. Preferred recrystallization solvents are aqueous ethanol and aqueous acetone. Most preferred recrystallization solvent is aqueous acetone.

In case of employing an aqueous organic solvent as a recrystallization solvent, yields of the objective compound are affected by water content in recrystallization organic solvent. Preferred water content lies in the range of 10 to 30% (V/V%). Most preferred water content lies in the range of 10 to 25% (V/V%).

4-(1-Imidazolylmethyl)cinnamic acid hydrochloride used as a starting material is well known and can be prepared according to the method disclosed in U.S. Pat. No. 4,226,878. That is, said compound can be prepared by reacting sodium salt of imidazole with ethyl p-bromomethylcinnamate in acetonitrile and by hydrolyzing the reaction product with sodium hydroxide and then treating the resulting product with hydrochloric acid.

The above recrystallization is carried out preferably by the following procedure.

4-(1-Imidazolylmethyl)cinnamic acid hydrochloride is dissolved by heating in an adequate amount of 50% (V/V%) aqueous acetone and filtrated and the filtrate is diluted with acetone in an amount sufficient to make an aqueous solution of acetone having water content of about 10–30% (V/V%), preferably about 17% (V/V%). The mixture is allowed to stand at room temperature for an adequate period of time. The precipitates are collected and dried under reduced pressure at room temperature to obtain 4-(1-imidazolylmethyl)cinnamic acid hydrochloride monohydrate.

The $LD_{50}$ value of this compound is in oral administration to a rat is 6000 mg/kg or more.

The compounds can be administered in various forms according to the purposed therapy. Typical dosage forms which can be used are tablets, pills, powders, liquid preparations, suspensions, emulsions, granules, capsules, suppositories and injectable preparations.

In molding the pharmaceutical composition into a tablet form, a wide variety of conventional carriers known in this art can be used. Examples of suitable carriers are excipients such as glucose, lactose, starch, cacao butter, hardened vegetable oils, kaolin and talc, binders such as gum arabic powder, tragacanth powder, and ethanol, and disintegrants such as laminaria and agar. The tablets, if desired, can be coated to make sugar-coated tablets, gelatin-coated tablets, enteric-coated tablets, film-coated tablets, or tablets coated with two or more layers.

When the pharmaceutical composition is formulated into an injectable preparation, the resulting solution and suspension are preferably sterilized, and are isotonic with respect to the blood. In formulating the pharmaceutical composition into the form of a solution or suspension, any types of diluents customarily used in the art can be used. Examples of suitable diluents are water, ethyl alcohol, propylene glycol, polyoxyethylene sorbitol, and sorbitan esters. Sodium chloride, glucose or glycerol may be incorporated into a therapeutic agent in an amount sufficient to prepare an isotonic solution. The therapeutic agent may further contain ordinary dissolving aids, buffers, pain-alleviating agents, and preservatives, and optionally, coloring agents, perfumes, flavors, sweeteners and other drugs.

The dosage of the compound of this invention can be about 1 mg to 1,000 mg/body by oral administration, or about 0.1 mg to 100 mg/body by parenteral administration per day for adult human in multiple doses depending upon the disease which is being treated.

This invention is further illustrated in more detail by way of the following examples wherein the melting point of the product obtained are uncorrected. Unless otherwise indicated, all parts, percents, ratios and the like are by weight.

REFERENCE EXAMPLE 1

To a suspension of 0.96 g of 50% sodium hydride in 50 ml of dry acetonitrile was added 1.3 g of imidazole at room temperature, and then the mixture was stirred for 30 min. A solution of 5.38 g of ethyl p-bromomethylcinnamate in 20 ml of dry acetonitrile was added to the mixture at room temperature for 10 min, and then the mixture was stirred at the same temperature for 1 hr. After concentration under reduced pressure, the residue was dissolved in 100 ml of benzene and washed with water and dried. The solvent was evaporated and the residual oil was chromatographed on silica gel using chloroform, and the resulting crystals were recrystallized from diethyl ether to give 3.4 g of ethyl 4-(1-imidazolylmethyl)cinnamate. This compound was added to 30 ml of 80% aqueous ethanol containing 0.8 g of sodium hydroxide and the mixture was stirred for 4 hr at room temperature. After concentration and reduced pressure, 25 ml of water was added to the residue and the mixture was washed with diethyl ether. The mixture was adjusted to pH 1 to 2 by an addition of concentrated hydrochloric acid and the acidic solution was concentrated under reduced pressure. To the residue, 30 ml of 2-methyl-2-propanol was added and the mixture was evaporated again, and the residue was dissolved in 80 ml of ethanol and the insoluble materials were filtered off. The filtrate was evaporated to obtain 3.4 g of crude 4-(1-imidazolylmethyl)cinnamic acid hydrochloride.

EXAMPLE 1

In 35 ml of water, 10 g of 4-(1-imidazolylmethyl)cinnamic acid hydrochloride was dissolved by heating and the solution was allowed to stand overnight at room temperature. The resulting precipitates were collected by filtration and dried at room temperature under reduced pressure to obtain 6 g of 4-(1-imidazolylmethyl)cinnamic acid hydrochloride monohydrate.

melting point: 227°–228° C.

IR-absorption spectrum (KBr): $\nu$OH: 3270 cm$^{-1}$; $\nu$CO: 1705, 1685 cm$^{-1}$; $\nu$C=C: 1635 cm$^{-1}$.

NMR spectrum (DMSO-$d_6$); δ: 5.61(s,2H), 6.58(d,1H), 7.4–8.0(m,7H), 9.50(m,1H).

| Elemental analysis as $C_{13}H_{15}N_2O_3Cl$ | | | |
|---|---|---|---|
| | C % | H % | N % |
| Calcd. | 55.22 | 5.35 | 9.91 |
| Found | 55.01 | 5.28 | 9.83 |

EXAMPLE 2

In 60 ml of aqueous solution of acetone having water content of 25% (V/V%), 10 g of 4-(1-imidazolylmethyl)cinnamic acid hydrochloride was dissolved by heating and then the solution was allowed to stand overnight at room temperature. The resulting precipitates were collected by filtration and dried at room temperature for 3 hr under reduced pressure to obtain 7.0 g of 4-(1-imidazolylmethyl)cinnamic acid hydrochloride monohydrate. This product had the same IR-absorption spectrum and NMR spectrum as those of the product of EXAMPLE 1.

EXAMPLE 3

In 30 ml of 50% (V/V%) aqueous acetone 10 g of 4-(1-imidazolylmethyl)cinnamic acid hydrochloride was dissolved by heating and the solution was filtrated and then 60 ml of acetone was added to the filtrate. The mixture was allowed to stand overnight at room temperature. The resulting precipites were collected by filtration and dried at room temperature for 3 hr under reduced pressure to obtain 8.5 g of 4-(1-imidazolylmethyl)cinnamic acid hydrochloride monohydrate. This product had the same IR-absorption spectrum and NMR spectrum as those of the product of EXAMPLE 1.

FORMULATION EXAMPLE 1

4-(1-Imidazolylmethyl)cinnamic acid hydrochloride monohydrate, lactose, carboxymethylcellulose calcium, crystalline cellulose and calcium stearate were blended at a ratio of 100:48:10:40:2, respectively, and the mixture was compressed into tablets of 200 mg in weight.

Each tablet contains the following ingredients:
4-(1-imidazolylmethyl)cinnamic acid hydrochloride monohydrate: 100 mg
lactose: 48 mg
carboxymethylcellulose calcium: 10 mg
crystalline cellulose: 40 mg
calcium stearate: 2 mg.

FORMULATION EXAMPLE 2

4-(1-Imidazolylmethyl)cinnamic acid hydrochloride monohydrate, lactose and talc were blended at a ratio of 100:895:5, respectively, and the mixture was sieved to get particles of not more than 350μ for the preparation of powder.

The proportion of the ingredients in one gram of the powder is as follows:
4-(1-imidazolylmethyl)cinnamic acid hydrochloride monohydrate: 100 mg
lactose: 895 mg
talc: 5 mg.

FORMULATION EXAMPLE 3

4-(1-Imidazolylmethyl)cinnamic acid hydrochloride monohydrate, lactose, D-mannitol, hydroxypropylcellulose and talc were blended at a ratio of 100:675:200:20:5, respectively, and the mixture was granulated.

The proportion of the ingredients in one gram of the granule is as follows:
4-(1-imidazolylmethyl)cinnamic acid hydrochloride monohydrate: 100 mg
lactose: 675 mg
D-mannitol: 200 mg
hydroxypropylcellulose: 20 mg
talc: 5 mg.

FORMULATION EXAMPLE 4

4-(1-Imidazolylmethyl)cinnamic acid hydrochloride monohydrate, crystalline cellulose, carboxymethylcellulose calcium, hydroxypropylcellulose, calcium stearate and talc were blended at a ratio of 100:40:15:2:3:10, respectively, and the mixture was charged into hard capsules containing 170 mg of all ingredients.

Each capsule contains the following ingredients:
4-(1-imidazolylmethyl)cinnamic acid hydrochloride monohydrate: 100 mg
carboxymethylcellulose calcium: 15 mg
crystalline cellulose: 40 mg
hydroxypropylcellulose: 2 mg
calcium stearate: 3 mg
talc: 10 mg.

FORMULATION EXAMPLE 5

50 g of 4-(1-imidazolylmethyl)cinnamic acid hydrochloride monohydrate, 17 g of sodium hydroxide, 80 g of aminoacetic acid and 5 g of citric acid were dissolved in 5 l of distilled water for injections and the solution was filled into amples by 5 ml each. After filled up with nitrogen gas, the amples were sealed by fusion and sterilized by heating.

Each ample contains the following ingredients:
4-(1-imidazolylmethyl)cinnamic acid hydrochloride monohydrate: 50 mg
sodium hydroxide: 17 mg
aminoacetic acid: 80 mg
citric acid: 5 mg
distilled water: 5 ml.

EXAMPLE 4

Inhibition of Cerebral Infarction Caused by Arachidonic Acid

The right external carotid artery of a male rabbit weighing about 2 kg was ligated, a cannula was inserted in the reverse direction, and arachidonic acid was infused into the right internal carotid artery at a rate of 1 mg/animal/min. for 25 minutes, without blocking the blood flow.

4-(1-Imidazolylmethyl)cinnamic acid hydrochloride monohydrate and acetylsalicylic acid as an active control were orally administered respectively, 90 minutes before arachidonic acid infusion.

On the next day, the animal was sacrificed with pentobarbital (i.v.), the brain was taken out and macroscopically examined for infarction sites.

| COMPOUND | number of infarction / number of animals tested |
|---|---|
| control | 27/32 |
| 4-(1-imidazolylmethyl)cinnamic acid hydrochloride monohydrate | 4/10 |
| acetylsalicylic acid | 4/10 |

What is claimed is:

1. The compound of the formula:

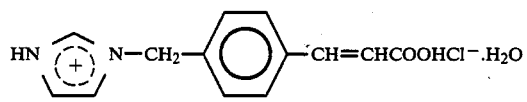

2. A pharmaceutical composition for alleviating diseases caused by thromboxane $A_2$ in mammals for oral administration containing, as an active ingredient, the compound of claim 1 in an amount in the range of about 1 to about 1000 mg per day per body in combination with a pharmaceutically acceptable carrier or diluent.

3. A pharmaceutical composition for alleviating diseases caused by trhomboxane $A_2$ in mammals for parenteral administration containing, as an active ingredient, the compound of claim 1 in an amount in the range of about 0.1 to about 100 mg per day per body in combination with a pharmaceutically acceptable carrier or diluent.